(12) United States Patent
Watts et al.

(10) Patent No.: US 11,154,210 B2
(45) Date of Patent: Oct. 26, 2021

(54) METHOD OF DETERMINING VASOREACTIVITY USING INHALED NITRIC OXIDE

(71) Applicant: VERO BIOTECH LLC, Atlanta, GA (US)

(72) Inventors: Tammy Watts, Palm Bay, FL (US); Robert F. Roscigno, Melbourne Beach, FL (US); David H. Fine, Cocoa Beach, FL (US); Lewis J. Rubin, La Jolla, CA (US)

(73) Assignee: VERO Biotech LLC, Atlanta, GA (US)

( * ) Notice: Subject to any disclaimer, the term of this patent is extended or adjusted under 35 U.S.C. 154(b) by 215 days.

(21) Appl. No.: 13/735,558

(22) Filed: Jan. 7, 2013

(65) Prior Publication Data

US 2013/0309328 A1 Nov. 21, 2013

Related U.S. Application Data

(63) Continuation of application No. 13/480,073, filed on May 24, 2012, now abandoned.

(60) Provisional application No. 61/490,929, filed on May 27, 2011.

(51) Int. Cl.
| | | |
|---|---|---|
| *A61K 31/13* | (2006.01) | |
| *A61B 5/026* | (2006.01) | |
| *A61K 33/00* | (2006.01) | |
| *A61M 16/12* | (2006.01) | |

(52) U.S. Cl.
CPC ............. *A61B 5/026* (2013.01); *A61K 31/13* (2013.01); *A61K 33/00* (2013.01); *A61M 16/12* (2013.01)

(58) Field of Classification Search
CPC ........ A61K 31/13; A61K 33/00; A61B 5/026; A61M 16/12
See application file for complete search history.

(56) References Cited

U.S. PATENT DOCUMENTS

| | | |
|---|---|---|
| 6,758,214 B2 | 7/2004 | Fine et al. |
| 7,025,869 B2 | 4/2006 | Fine et al. |
| 7,040,313 B2 | 5/2006 | Fine et al. |
| 7,560,076 B2 | 7/2009 | Rounbehler et al. |
| 7,618,594 B2 | 11/2009 | Rounbehler et al. |
| 7,914,743 B2 | 3/2011 | Fine et al. |
| 7,947,227 B2 | 5/2011 | Fine et al. |
| 8,057,742 B2 | 11/2011 | Rounbehler et al. |
| 8,066,904 B2 | 11/2011 | Fine et al. |
| 8,083,997 B2 | 12/2011 | Rounbehler et al. |
| 8,173,072 B2 | 5/2012 | Fine et al. |
| 8,187,544 B2 | 5/2012 | Fine et al. |
| 8,211,368 B2 | 7/2012 | Fine et al. |
| 8,221,800 B2 | 7/2012 | Fine et al. |
| 8,226,916 B2 | 7/2012 | Rounbehler et al. |
| 8,246,725 B2 | 8/2012 | Rounbehler et al. |
| 8,268,252 B2 | 9/2012 | Fuller et al. |
| 8,282,966 B2 | 10/2012 | Baldassarre et al. |
| 8,371,296 B2 | 2/2013 | Fine et al. |
| D679,366 S | 4/2013 | Fuller |
| D688,352 S | 8/2013 | Fuller |
| 8,607,785 B2 | 12/2013 | Fine et al. |
| 8,609,026 B2 | 12/2013 | Fine et al. |
| 8,609,028 B2 | 12/2013 | Rounbehler et al. |
| 8,613,958 B2 | 12/2013 | Fine |
| 8,646,445 B2 | 2/2014 | Fine et al. |
| 8,701,657 B2 | 4/2014 | Fine et al. |
| 8,715,577 B2 | 5/2014 | Fine et al. |
| 8,741,222 B2 | 6/2014 | Fine et al. |
| 8,821,801 B2 | 9/2014 | Rounbehler et al. |
| 8,887,720 B2 | 11/2014 | Fine et al. |
| 8,944,049 B2 | 2/2015 | Fine et al. |
| 9,192,718 B2 | 11/2015 | Fine |
| 9,408,994 B2 | 8/2016 | Fine et al. |
| 9,522,249 B2 | 12/2016 | Rounbehler et al. |
| 9,604,028 B2 | 3/2017 | Fine et al. |
| 9,701,538 B2 | 7/2017 | Fine et al. |
| 9,956,373 B2 | 5/2018 | Rounbehler et al. |
| 10,081,544 B2 | 9/2018 | Fine et al. |
| 10,086,352 B2 | 10/2018 | Fine et al. |
| 10,124,142 B2 | 11/2018 | Rounbehler et al. |
| 10,179,222 B2 | 1/2019 | Fine et al. |
| 10,213,572 B2 | 2/2019 | Gellman et al. |
| 10,737,051 B2 | 8/2020 | Gellman et al. |

(Continued)

FOREIGN PATENT DOCUMENTS

| | | |
|---|---|---|
| JP | 2008-523090 | 7/2008 |
| JP | 2011-010865 | 1/2011 |

(Continued)

OTHER PUBLICATIONS

Oudiz et al ("Cardiac Catheterization in Pulmonary Artedal Hypertension: An Updated Guide to Proper Use", Advances in Pulmonary Hypertension: Official Journal of the Pulmonary Hypertension Association, 2005, vol. 4, No. 3, pp. 15-25).*

Krasuski et al ("The response to inhaled nitric oxide in patients with pulmonary artery hypertension is not masked by baseline vasodilator use," Am Heart J 2005;150:725-8).*

Humbert, M., et al., "Treatment of Pulmonary Arterial Hypertension," N. Engl. J. Med. 351: 1425-1436 (2004). (Year: 2004).*

Safdar, Z., Respiratory Medicine 105:818-827 (Jan. 26, 2011). (Year: 2011).*

International Search Report dated Aug. 17, 2012, issued in International Application No. PCT/US2012/039401.

Written Opinion of the International Searching Authority dated Aug. 17, 2012, issued in International Application No. PCT/US2012/039401.

(Continued)

*Primary Examiner* — David J Blanchard
*Assistant Examiner* — Daniel F. Coughlin

(57) ABSTRACT

A method for treating pulmonary arterial hypertension in a patient can include determining whether a patient with pulmonary arterial hypertension has an enlarged right ventricle or right ventricular dysfunction, where the patient has previously been administered a prostanoid and weaning the patient off of the prostanoid if the patient does not have an enlarged right ventricle or right ventricular dysfunction.

4 Claims, 1 Drawing Sheet

(56) References Cited

U.S. PATENT DOCUMENTS

| | | |
|---|---|---|
| 10,780,241 B2 | 9/2020 | Fine et al. |
| 10,814,092 B2 | 10/2020 | Rounbehler et al. |
| 10,926,054 B2 | 2/2021 | Fine et al. |
| 10,960,168 B2 | 3/2021 | Fine et al. |
| 11,000,484 B2 | 5/2021 | Fine |
| 2009/0197922 A1 | 8/2009 | Maitland et al. |
| 2010/0130500 A1 | 5/2010 | Kakkis |
| 2012/0093948 A1 | 4/2012 | Fine et al. |

FOREIGN PATENT DOCUMENTS

| | | |
|---|---|---|
| WO | WO 2006/063215 | 6/2006 |
| WO | WO 2011/002606 | 1/2011 |
| WO | 2011/063335 A1 | 5/2011 |
| WO | WO 2011/063335 A1 * | 5/2011 |
| WO | WO 2012/075420 | 6/2012 |
| WO | WO 2012/151701 | 11/2012 |
| WO | WO 2012/166534 | 12/2012 |

OTHER PUBLICATIONS

Notification Concerning Transmittal of International Preliminary Report on Patentability (Chapter I of the Patent Cooperation Treaty) dated Dec. 12, 2013, issued in International Application No. PCT/US2012/039401.

Oudiz et al. Cardiac Catheterization in Pulmonary Arterial Hypertension: An Updated Guide to Proper Use. Advances in Pulmonary Hypertension: Official Journal of the Pulmonary Hypertension Association, 2005, vol. 4, pp. 15-25; .specially p. 22, col. 1, para 6 and col. 2, para 4-5; p. 24, col. 1, para 1-3.

Melnick, Laura, "Effective of Transition from Intravenous Epoprostenol to Oral/Inhaled Targeted Pulmonary Arterial Hypertension Therapy in Pediatric Idiopathic and Familial Pulmonary Arterial Hypertension," American Journal of Cardiology (2010) vol. 105, No. 10, pp. 1485-1489.

English Translation Office Action in Japanese Patent Application No. 2017-061811 dated Jan. 25, 2018.

Office Action in Japanese Patent Application No. 2017-061811 dated Oct. 28, 2018.

Examination Report No. 1 for Australian Application No. 2012262534, dated May 14, 2015, 4 pages.

Office Action for Canadian Application No. 2,837,341, dated Jun. 19, 2019, 4 pages.

Office Action for European Application No. 12793863.7, dated Mar. 20, 2017, 7 pages.

Office Action for European Application No. 12793863.7, dated May 18, 2016, 5 pages.

Extended European Search Report for European Application No. 12793863.7, dated Feb. 24, 2015, 8 pages.

Supplementary Partial European Search Report for European Application No. 12793863.7, dated Nov. 27, 2014, 6 pages.

Notice of Reasons for Refusal for Japanese Application No. 2014-512110, dated Feb. 23, 2016, 10 pages.

Decision of Refusal for Japanese Application No. 2014-512110, dated Nov. 29, 2016, 8 pages.

Notice of Reasons for Refusal for Japanese Application No. 2017-061811, dated Nov. 28, 2017, 10 pages.

Notice off Reasons for Refusal for Japanese Application No. 2017-061811, dated Apr. 9, 2019, 6 pages.

Notice of Reasons for Refusal for Japanese Application No. 2019-035311, dated Mar. 3, 2020, 5 pages.

Nauser, T. D. et al., "Diagnosis and treatment of pulmonary hypertension," American Family Physician, vol. 63, No. 9. pp. 1789-1798 (May 2001).

Japanese Circulation Journal, No. 1385, vol. 59, Suppl. I, pp. 391 (1995).

* cited by examiner

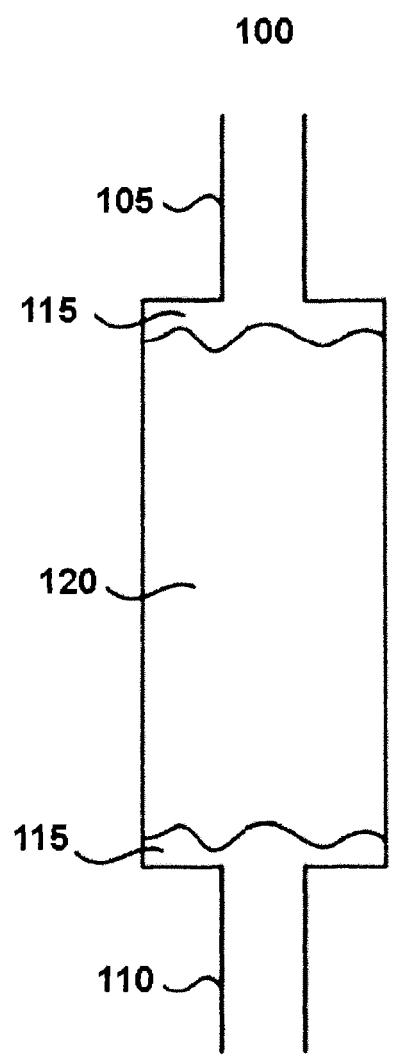

METHOD OF DETERMINING VASOREACTIVITY USING INHALED NITRIC OXIDE

CLAIM OF PRIORITY

This application is a continuation of U.S. Ser. No. 13/480,073, filed on May 24, 2012, which claims the benefit of prior U.S. Provisional Application No. 61/490,929 filed on May 27, 2011, each of which is incorporated by reference in its entirety.

TECHNICAL FIELD

This description relates to methods of determining vasoreactivity using inhaled nitric oxide.

BACKGROUND

Nitric oxide (NO), also known as nitrosyl radical, is a free radical that is an important signalling molecule. For example, NO can cause smooth muscles in blood vessels to relax, thereby resulting in vasodilation and increased blood flow through the blood vessel. These effects can be limited to small biological regions since NO can be highly reactive with a lifetime of a few seconds and can be quickly metabolized in the body.

Generally, nitric oxide (NO) can be inhaled or otherwise delivered to an individual's lungs. Providing a dose of NO can result in localized pulmonary vasodilation. Typically, the NO gas can be supplied in a bottled gaseous form diluted in another gas, for example, nitrogen gas ($N_2$). Great care should be taken to prevent the presence of even trace amounts of oxygen ($O_2$) in the tank of NO gas because the NO, in the presence of $O_2$, can be oxidized to nitrogen dioxide ($NO_2$). Unlike NO, the part per million levels of $NO_2$ gas can be highly toxic if inhaled and can form nitric and nitrous acid in the lungs.

SUMMARY

In one aspect, a method for treating pulmonary arterial hypertension in a patient can include determining whether a patient with pulmonary arterial hypertension has an enlarged right ventricle or right ventricular dysfunction.

In some embodiments, the patient has previously been administered a prostanoid. A prostanoid can include a prostaglandin, a prostaglandin derivative or a thromboxane. A prostanoid can include prostacyclin, epoprostenol, treprostinil, iloprost orberaprost. A prostanoid can be administered intravenously, subcutaneously, orally (e.g. liquid, tablet or capsule) or by inhalation. A patient can be administered a prostanoid as part of a treatment course. A course can include administration of the prostanoid at least once a day, at least once a week or at least once a month. A course can last for at least three months, at least six months, at least one year, at least two years, or more than two years.

In some embodiments, a patient can be a neonate (i.e. less than one month old), an infant (at least one month to one year old) or a toddler (at least one year to three years old). In other embodiments, a patient can be a child (at least three years to 18 years old). More specifically, a patient can be a young child (at least three years to seven years old). In still other embodiments, a patient can be an adult (at least 18 years old).

In some embodiments, determining if the patient has an enlarged right ventricle or right ventricular dysfunction can include administering a vasoactive agent to the patient. A vasoactive agent can cause vasculature to dilate, increasing the internal diameter of the vasculature. In some embodiments, a vasoactive agent can be inhaled nitric oxide.

In some embodiments, administering inhaled nitric oxide can include communicating an air flow including nitrogen dioxide through a receptacle. The receptacle can include an inlet, an outlet, and/or a surface-active material.

In some embodiments, a surface-active material can include a reducing agent. Any appropriate reducing agent that can convert $NO_2$ or $N_2O_4$ to NO can be used as determined by a person of skill in the art. For example, a reducing agent can include a hydroquinone, glutathione, thiols, nitrites, and/or one or more reduced metal salts such as Fe(II), Mo(VI), NaI, Ti(III) or Cr(III). A reducing agent can be an antioxidant. An antioxidant can be an aqueous solution of an antioxidant. A antioxidant can be ascorbic acid, alpha tocopherol, or gamma tocopherol. Any appropriate antioxidant can be used depending on the activities and properties as determined by a person of skill in the art. An antioxidant can be used dry or wet. A surface-active material can be coated with a reducing agent or coated with an aqueous solution of a reducing agent.

In some embodiments an inlet can be configured to receive the flow of nitrogen dioxide.

In some embodiments, administering nitric oxide can include communicating the air flow to the outlet through the surface-active material.

In some embodiments, administering nitric oxide can include converting the gaseous nitrogen dioxide to nitric oxide, most preferably, at ambient temperature.

In some embodiments, a vasoactive agent can be administered repeatedly. In some embodiments, a vasoactive agent can be administered at least twice, at least three times, at least four times, at least five times, at least ten times or greater than ten times.

In some embodiments, determining whether the patient has an enlarged right ventricle or right ventricular dysfunction can include monitoring an at least one indicator of hemodynamics of the patient. Monitoring at least one indicator can include measuring a hemodynamic property. For example, a hemodynamic property or an at least one indicator can include pulmonary vascular resistance, mean pulmonary arterial pressure or cardiac output. Hemodynamics can be anything relating to the movement, flow or circulation of blood. An indicator of hemodynamics can include, but is not limited to, a pressure, a volume or a rate.

Monitoring an at least one indicator can include monitoring at any time point during a method. In some embodiments, monitoring can include monitoring the at least one indicator of the hemodynamics of the patient before administering a vasoactive agent to the patient. In some embodiments, monitoring can include monitoring the at least one indicator of the hemodynamics of the patient after administering a vasoactive agent to the patient.

In some embodiments, determining whether the patient has an enlarged right ventricle or right ventricular dysfunction can include calculating a change in at least one indicator of the hemodynamics of the patient between before the inhaled nitric oxide was administered and after the inhaled nitric oxide was administered. For example, an at least one indicator of the hemodynamics of the patient can be monitored before administration of a vasoactive agent and then the at least one indicator of the hemodynamics of the patient can be monitored after administration of a vasoactive agent. The difference between the indicator of the hemodynamics of the patient can be determined or calculated based on at least those two time points. A change in at least one indicator of the hemodynamics of the patient can be a negative value, zero or a positive value.

In some embodiments, the at least one indicator of hemodynamics can include pulmonary vascular resistance and cardiac output. In some embodiments, determining whether the patient has an enlarged right ventricle or right ventricular dysfunction can include determining the presence of an increase in cardiac output after administration of nitric oxide which correlates with a decrease in pulmonary vascular resistance after administration of nitric oxide. For example, a minimal decrease in pulmonary vascular resistance can correlate with a minimal increase in cardiac output. Accordingly, a moderate decrease in pulmonary vascular resistance can correlate with a moderate increase in cardiac output, and a marked decrease in pulmonary vascular resistance can correlate with a marked increase in cardiac output. A minimal decrease in pulmonary vascular resistance can be a decrease of at least zero mmHg·min/l and at most 0.2 mmHg·min/l, a moderate decrease in pulmonary vascular resistance can be a decrease of at least 0.2 mmHg·min/l and at most 1.0 mmHg·min/l, and a marked decrease can be of at least 1.0 mmHg·min/l. A pulmonary vascular resistance can also increase. A minimal increase in cardiac output can be at least 0.0 l/min to at most 0.1 l/min, a moderate increase in cardiac output can be at least 0.1 l/min to at most 0.3 l/min, a marked increase in cardiac output can be at least 0.3 l/min. Also, cardiac output can decrease.

In some embodiments, a decrease of at least 0.2 mmHg·min/l in pulmonary vascular resistance can correlate with an increase of at least 0.1 l/min in cardiac output.

In some embodiments, a statistically significant decrease in pulmonary vascular resistance can correlate with a statistically significant increase in cardiac output. Statistical significance can be independent of the magnitude of change (i.e. minimal, moderate, marked). Statistical significance can be determined using any of a variety of statistical tests known to those of skill in the art, including but not limited to, chi-square test, student's t-test, z-test, Fisher's exact test, runs test, Kolmogorov-Smirnov test, Mann-Whitney U test, Wald-Wolfowitz runs, Kruskal-Wallis test, Jonckheere-Terpstra test, McNemar test, Wilcoxon sign test, Friedman test, Kendall's W test and Cochran Q test.

In some embodiments, an increase in cardiac output which correlates with a decrease in pulmonary vascular resistance can indicate that an enlarged right ventricle or right ventricular dysfunction may not be present. A decrease in pulmonary vascular resistance can occur as a result of vasodilation. Therefore, as pulmonary vascular resistance decreases, a correlative increase in cardiac output can be expected, particularly when the right ventricle is functioning properly. On the other hand, a decrease in pulmonary vascular resistance without a correlative cardiac output can indicate that the right ventricle is unable to respond in the change in the hemodynamics and can suggest an enlarged right ventricle or right ventricular dysfunction.

In some embodiments, the method can include weaning the patient off of the prostanoid if the patient does not have an enlarged right ventricle or right ventricular dysfunction. Weaning can mean the decreasing the amount of prostanoid administered over time to a patient during a given unit of time (e.g. per day, per week, per month), most preferably, decreasing the amount to zero.

In another aspect, a method for treating pulmonary arterial hypertension in a patient can include administering a vasoactive agent to a patient with pulmonary arterial hypertension. The patient may have previously been administered a prostanoid. A prostanoid can include a prostaglandin, a prostaglandin derivative or a thromboxane. A prostanoid can include prostacyclin, epoprostenol, trepostinil, iloprost or beraprost. A prostanoid can be administered intravenously, subcutaneously, orally (e.g. liquid, tablet or capsule) or by inhalation. A patient can be administered a prostanoid as part of a treatment course. A course can include administration of the prostanoid at least once a day, at least once a week or at least once a month. A course can last for at least three months, at least six months, at least one year, at least two years, or more than two years.

In some embodiments, a patient can be a neonate (i.e. less than one month old), an infant (at least one month to one year old) or a toddler (at least one year to three years old). In other embodiments, a patient can be a child (at least three years to 18 years old). More specifically, a patient can be a young child (at least three years to seven years old). In still other embodiments, a patient can be an adult (at least 18 years old).

In some embodiments, a method can include determining whether the patient demonstrates an acute vasodilator response to the vasoactive agent. A vasoactive agent can cause vasculature to dilate, increasing the internal diameter of the vasculature. In some embodiments, a vasoactive agent can be inhaled nitric oxide.

In some embodiments, administering inhaled nitric oxide can include communicating an air flow including nitrogen dioxide through a receptacle. The receptacle can include an inlet, an outlet, and/or a surface-active material.

In some embodiments, a surface-active material can include a reducing agent. Any appropriate reducing agent that can convert $NO_2$ or $N_2O_4$ to NO can be used as determined by a person of skill in the art. For example, a reducing agent can include a hydroquinone, glutathione, thiols, nitrites, and/or one or more reduced metal salts such as Fe(II), Mo(VI), NaI, Ti(III) or Cr(III). A reducing agent can be an antioxidant. An antioxidant can be an aqueous solution of an antioxidant. A antioxidant can be ascorbic acid, alpha tocopherol, or gamma tocopherol. Any appropriate antioxidant can be used depending on the activities and properties as determined by a person of skill in the art. An antioxidant can be used dry or wet. A surface-active material can be coated with a reducing agent or coated with an aqueous solution of a reducing agent.

In some embodiments an inlet can be configured to receive the flow of nitrogen dioxide.

In some embodiments, administering nitric oxide can include communicating the air flow to the outlet through the surface-active material.

In some embodiments, administering nitric oxide can include converting the gaseous nitrogen dioxide to nitric oxide, most preferably, at ambient temperature.

In some embodiments, a vasoactive agent can be administered repeatedly. In some embodiments, a vasoactive agent can be administered at least twice, at least three times, at least four times, at least five times, at least ten times or greater than ten times.

In some embodiments, determining whether the patient demonstrates an acute vasodilator response to the vasoactive agent can include monitoring an at least one indicator of hemodynamics of the patient. Monitoring at least one indicator can include measuring a hemodynamic property. For example, a hemodynamic property or an at least one indicator can include pulmonary vascular resistance, mean pulmonary arterial pressure or cardiac output. Hemodynamics can be anything relating to the movement, flow or circulation of blood. An indicator of hemodynamics can include, but is not limited to, a pressure, a volume or a rate.

Monitoring an at least one indicator can include monitoring at any time point during a method. In some embodiments, monitoring can include monitoring the at least one indicator of the hemodynamics of the patient before administering a vasoactive agent to the patient. In some embodiments, monitoring can include monitoring the at least one indicator of the hemodynamics of the patient after administering a vasoactive agent to the patient.

In some embodiments, determining whether the patient demonstrates an acute vasodilator response to the vasoactive agent can include calculating a change in at least one indicator of the hemodynamics of the patient between before the vasoactive was administered and after the vasoactive was administered. For example, an at least one indicator of the hemodynamics of the patient can be monitored before administration of a vasoactive agent and then the at least one indicator of the hemodynamics of the patient can be monitored after administration of a vasoactive agent. The difference between the indicator of the hemodynamics of the patient can be determined or calculated based on at least those two time points. A change in at least one indicator of the hemodynamics of the patient can be a negative value, zero or a positive value.

In some embodiments, the at least one indicator of hemodynamics can include mean pulmonary arterial pressure. In some embodiments, determining whether the patient demonstrates an acute vasodilator response to the vasoactive agent can include determining the presence of a change in mean pulmonary arterial pressure of greater than 5 mm Hg, greater than 10 mm Hg between, greater than 12 mm Hg or greater than 15 mm Hg before the inhaled nitric oxide was administered and after the inhaled nitric oxide was administered.

In some embodiments, the method can include weaning the patient off of the prostanoid if the patient demonstrates an acute vasodilator response to the vasoactive agent. Weaning can mean the decreasing the amount of prostanoid administered over time to a patient during a given unit of time (e.g. per day, per week, per month), most preferably, decreasing the amount to zero.

In another aspect, a method for monitoring a patient with pulmonary arterial hypertension can include performing a vasoreactivity challenge test.

In another aspect, a method for monitoring a patient with pulmonary arterial hypertension can include administering inhaled nitric oxide to the patient with pulmonary arterial hypertension.

In some embodiments, a patient can be a neonate (i.e. less than one month old), an infant (at least one month to one year old) or a toddler (at least one year to three years old). In other embodiments, a patient can be a child (at least three years to 18 years old). More specifically, a patient can be a young child (at least three years to seven years old). In still other embodiments, a patient can be an adult (at least 18 years old).

In some embodiments, administering inhaled nitric oxide can include communicating an air flow including nitrogen dioxide through a receptacle. The receptacle can include an inlet, an outlet, and/or a surface-active material.

In some embodiments, a vasoactive agent can be administered repeatedly. In some embodiments, a vasoactive agent can be administered at least twice, at least three times, at least four times, at least five times, at least ten times or greater than ten times.

In some embodiments, a surface-active material can include a reducing agent. Any appropriate reducing agent that can convert $NO_2$ or $N_2O_4$ to NO can be used as determined by a person of skill in the art. For example, a reducing agent can include a hydroquinone, glutathione, thiols, nitrites, and/or one or more reduced metal salts such as Fe(II), Mo(VI), NaI, Ti(III) or Cr(III). A reducing agent can be an antioxidant. An antioxidant can be an aqueous solution of an antioxidant. A antioxidant can be ascorbic acid, alpha tocopherol, or gamma tocopherol. Any appropriate antioxidant can be used depending on the activities and properties as determined by a person of skill in the art. An antioxidant can be used dry or wet. A surface-active material can be coated with a reducing agent or coated with an aqueous solution of a reducing agent.

In some embodiments an inlet can be configured to receive the flow of nitrogen dioxide.

In some embodiments, administering nitric oxide can include communicating the air flow to the outlet through the surface-active material.

In some embodiments, administering nitric oxide can include converting the gaseous nitrogen dioxide to nitric oxide, most preferably, at ambient temperature.

In some embodiments, a method can include monitoring an at least one indicator of hemodynamics of the patient. Monitoring at least one indicator can include measuring a hemodynamic property. For example, a hemodynamic property or an at least one indicator can include pulmonary vascular resistance, mean pulmonary arterial pressure or cardiac output. Hemodynamics can be anything relating to the movement, flow or circulation of blood. An indicator of hemodynamics can include, but is not limited to, a pressure, a volume or a rate.

Monitoring an at least one indicator can include monitoring at any time point during a method. In some embodiments, monitoring can include monitoring the at least one indicator of the hemodynamics of the patient before administering inhaled nitric oxide to the patient. In some embodiments, monitoring can include monitoring the at least one indicator of the hemodynamics of the patient after administering inhaled nitric oxide to the patient.

In another aspect, a method for diagnosing right ventricular dysfunction can include administering a vasoactive agent to a patient. A patient can be suspected of having right ventricular dysfunction. A patient can have been diagnosed with pulmonary arterial hypertension.

In some embodiments, a patient can be a neonate (i.e. less than one month old), an infant (at least one month to one year old) or a toddler (at least one year to three years old). In other embodiments, a patient can be a child (at least three years to 18 years old). More specifically, a patient can be a young child (at least three years to seven years old). In still other embodiments, a patient can be an adult (at least 18 years old).

In some embodiments, a vasoactive agent can be administered repeatedly. In some embodiments, a vasoactive agent can be administered at least twice, at least three times, at least four times, at least five times, at least ten times or greater than ten times.

In some embodiments, a vasoactive agent can be nitric oxide, more specifically, inhaled nitric oxide. In some embodiments, administering inhaled nitric oxide can include communicating an air flow including nitrogen dioxide through a receptacle. The receptacle can include an inlet, an outlet, and/or a surface-active material.

In some embodiments, a surface-active material can include a reducing agent. Any appropriate reducing agent that can convert $NO_2$ or $N_2O_4$ to NO can be used as determined by a person of skill in the art. For example, a reducing agent can include a hydroquinone, glutathione, thiols, nitrites, and/or one or more reduced metal salts such as Fe(II), Mo(VI), NaI, Ti(III) or Cr(III). A reducing agent can be an antioxidant. An antioxidant can be an aqueous solution of an antioxidant. A antioxidant can be ascorbic acid, alpha tocopherol, or gamma tocopherol. Any appropriate antioxidant can be used depending on the activities and properties as determined by a person of skill in the art. An antioxidant can be used dry or wet. A surface-active material can be coated with a reducing agent or coated with an aqueous solution of a reducing agent.

In some embodiments an inlet can be configured to receive the flow of nitrogen dioxide.

In some embodiments, administering nitric oxide can include communicating the air flow to the outlet through the surface-active material.

In some embodiments, administering nitric oxide can include converting the gaseous nitrogen dioxide to nitric oxide, most preferably, at ambient temperature.

In some embodiments, a method can include monitoring an at least one indicator of hemodynamics of the patient. Monitoring at least one indicator can include measuring a hemodynamic property. For example, a hemodynamic property or an at least one indicator can include pulmonary vascular resistance, mean pulmonary arterial pressure or cardiac output. Hemodynamics can be anything relating to the movement, flow or circulation of blood. An indicator of hemodynamics can include, but is not limited to, a pressure, a volume or a rate.

Monitoring an at least one indicator can include monitoring at any time point during a method. In some embodiments, monitoring can include monitoring the at least one indicator of the hemodynamics of the patient before administering a vasoactive agent to the patient. In some embodiments, monitoring can include monitoring the at least one indicator of the hemodynamics of the patient after administering a vasoactive agent to the patient.

In some embodiments, a method can include determining whether the patient has right ventricular dysfunction.

In some embodiments, the at least one indicator of hemodynamics can include pulmonary vascular resistance and cardiac output. In some embodiments, determining whether the patient has right ventricular dysfunction can include determining the presence of an increase in cardiac output after administration of nitric oxide which correlates with a decrease in pulmonary vascular resistance after administration of nitric oxide. For example, a minimal decrease in pulmonary vascular resistance can correlate with a minimal increase in cardiac output. Accordingly, a moderate decrease in pulmonary vascular resistance can correlate with a moderate increase in cardiac output, and a marked decrease in pulmonary vascular resistance can correlate with a marked increase in cardiac output. A minimal decrease in pulmonary vascular resistance can be a decrease of at least zero mmHg·min/l and at most 0.2 mmHg·min/l, a moderate decrease in pulmonary vascular resistance can be a decrease of at least 0.2 mmHg·min/l and at most 1.0 mmHg·min/l, and a marked decrease can be of at least 1.0 mmHg·min/l. A pulmonary vascular resistance can also increase. A minimal increase in cardiac output can be at least 0.0 l/min to at most 0.1 l/min, a moderate increase in cardiac output can be at least 0.1 l/min to at most 0.3 l/min, a marked increase in cardiac output can be at least 0.3 l/min. Also, cardiac output can decrease.

In some embodiments, a decrease of at least 0.2 mmHg·min/l in pulmonary vascular resistance can correlate with an increase of at least 0.1 l/min in cardiac output.

In some embodiments, a statistically significant decrease in pulmonary vascular resistance can correlate with a statistically significant increase in cardiac output. Statistical significance can be independent of the magnitude of change (i.e. minimal, moderate, marked). Statistical significance can be determined using any of a variety of statistical tests known to those of skill in the art, including but not limited to, chi-square test, student's t-test, z-test, Fisher's exact test, runs test, Kolmogorov-Smirnov test, Mann-Whitney U test, Wald-Wolfowitz runs, Kruskal-Wallis test, Jonckheere-Terpstra test, McNemar test, Wilcoxon sign test, Friedman test, Kendall's W test and Cochran Q test.

In some embodiments, an increase in cardiac output which correlates with a decrease in pulmonary vascular resistance can indicate that an enlarged right ventricle or right ventricular dysfunction may not be present. A decrease in pulmonary vascular resistance can occur as a result of vasodilation. Therefore, as pulmonary vascular resistance decreases, a correlative increase in cardiac output can be expected, particularly when the right ventricle is functioning properly. On the other hand, a decrease in pulmonary vascular resistance without a correlative cardiac output can indicate that the right ventricle is unable to respond in the change in the hemodynamics and can suggest an enlarged right ventricle or right ventricular dysfunction.

Other features will become apparent from the following detailed description, taken in conjunction with the accompanying drawings, which illustrate by way of example, the features of the various embodiments.

BRIEF DESCRIPTION OF THE DRAWINGS

FIG. 1 is a diagram of a NO delivery system.

DETAILED DESCRIPTION

Introduction

Pulmonary arterial hypertension (PAH), a rare progressive disorder, can carry a poor prognosis. PAH can be associated with significant morbidity and mortality, having a historical survival rate rarely exceeding 5 years. Patients with PAH can be classified based on a system developed by the World Health Organization (WHO), which places patients in one of four classes based on aetiology. (Nauser, et al., "Diagnosis and Treatment of Pulmonary Hypertension," Am Fam Physician, 2001; 63: 1789-98, 1800, which is incorporated by reference in its entirety). Patients can also be classified using a Functional classification system. (Nauser, 2001).

The use of parenteral prostacyclin analogs, the first medications approved for the treatment of PAH, has resulted in substantial improvement in survival for PAH WHO functional class III and IV patients. However, treatment with prostacyclin analogs can be costly and complex to administer, can require continuous infusion, and can be associated with frequent side effects (e.g., flushing, jaw pain, diarrhea) and a potential for severe or life-threatening sequelae (e.g., catheter-related infections and sepsis). Also, significant, potentially life-threatening, hemodynamic compromise may occur due to abrupt cessation of the infusion. The complications associated with parenteral prostacyclin therapy can include reduced quality of life, increased hospitalizations, morbidity and in certain cases, can be life threatening.

Traditionally, initiating treatment with parenteral prostacyclin therapies can be a life-long requirement with no opportunity to consider alternative therapies that may be less invasive and less cumbersome. However, in the past decade significant advances in the treatment of PAH, along with a better understanding of the pathogenesis of this debilitating disease, suggest alternative patient management strategies may be available.

It has been suggested that PAH can become a "fixed" defect in the pulmonary vasculature with decreased reactivity to various vasodilators. The exact mechanism of decreased responsiveness to acute vasodilator testing is unknown. The propensity for select patients with PAH to have normalization of pulmonary hemodynamics following long-term administration of parenteral prostacyclin therapy is also unknown. However, some patients have demonstrated a normalization of pulmonary hemodynamics following long-term administration of parental prostacyclin therapy.

For example, one case study involving four WHO class IV patients reported successful transition from chronic parenteral prostacyclin infusion to less complex and less invasive treatment following normalization of pulmonary pressures and restored pulmonary vasoreactivity (improving to WHO class I-II). (Kim et al., 2003).

Following this single center experience, additional successes have been reported, documenting a total of 63 transitions from prostanoid therapy to alternative therapies. (Sidhu, et al., 2011; Johnson, et al., 2007; Steiner, et al., 2006; Diaz-Guzman, et al., 2008; Suleman, et al., 2004; Camacho, et al., 2006). Table 1 summarizes the available literature from parenteral prostacyclin therapy to oral agents.

Predictors of successful transition remain difficult to identify because of the variety of detail reported in the literature, the retrospective nature of the experiences, the population baseline characteristics, and the inconsistent methodologies for collecting data across the reported single center experiences, for example. This can make it difficult to draw any conclusions from the reports. Additionally, the transition process can be a complex process that can require careful monitoring and close follow-up.

However, common criteria has been noted for selecting patients for transition from prostanoid therapy to alternative therapies. The common criteria can include that a patient is considered "clinically stable." A patient can be considered "clinically stable" if the patient is on stable doses of prostanoid analogs, has no evidence of overt right-sided heart failure, and/or is in WHO classes I-III. While classes I-III have shown evidence of being capable of transition,

TABLE 1

Transition From Parenteral Prostacyclins to Oral Agents: Summary of Available Literature

|  | Kim, et al. | Suleman and Frost | Steiner, et al. | Johnson, et al | Diaz-Guzman | Sidhu | Camacho |
|---|---|---|---|---|---|---|---|
| # of Patients | 4 | 23 | 22 | 15 | 21 | 7 | 5 |
| % Success | 4 (100%) | 11 (47.8%) | 7 (31.8%) | 10 (66.6%) | 15 (71.4%) | 6 | 5 (100%) |
| Design | Retrospective | Prospective | Prospective | Retrospective | Retrospective | Retrospective | Prospective |
| Wean Criteria | Normalization of PAP | In frequent increase PGI2 dose, FC II, III no heart failure | Stable FC, <10% decrease in 6MWD and no PGI2 dose changes | Stable FC, no increase in PGI2, oral therapy for 3 months | Stable FC I, II, or III, stable 6MWD, stable prostanoid dose, no right heart failure, oral therapy at least 2 months | Stable FC I, II | Stable, complications associated with PGI Tx |
| Mean PGI2 Duration (mos.) Success/Failed | 68.4 | 35.2/83.4 | 41/36 | 45.1 | 26/16 | 14 | 57 |
| Mean max PGI2 Dose (ng/kg/min Success/Failed At wean Success/Failed | 40.5/NR | 25.9/40.1 | 25.5/37.67 | 23.2/NR | 18/15.5 | 17/NR | 35/NR (+2 on Iloprost) |
| Mean 6MWD | N/A | 361.8 | 317.9/294 | 420 | 427.7/469.1 | 405 | 465 |
| mPAP | 21 | 65.8/84.1 | 38/56 | 35.8 | 38.2/42.8 |  | N/A |
| CI (L/min/m$^2$)/CO | CI-2.85 | CO-4.4/4.4 | N/A | CO4.9 | CI-2.1/1.9 | CI- | N/A |
| PVR (units) | N/A | N/A | N/A | 6.2 | 10.3/17.5 |  | N/A |
| Mean FU mo. | 11 | 9.6 | 17.7 | 29.9 | 27.3 | 41.3 | 17.6 |
| AE transition | None | 2 late failures, no deaths | 4 deaths; 2 Success 2 Failures | 2 late failures, no deaths | 2 deaths; 1 Success-pneumonia 1 Failure | 1 late failure | None |

NR = Not Reported

Sidhu, et al. has also reported the successful transition of functional class III-IV patients from prostanoid therapy to an alternative therapy. However, it is not clear if the functional class documented by Sidhu was determined at time of diagnosis or following prostanoid therapy.

Normalization of pulmonary pressures, restoration of pulmonary vasoreactivity, and/or clinical response to treatment can have significant implications regarding a patient's condition. These factors may prove to be valuable measures of treatment effect. These factors may also prove valuable for evaluating the extent or reversal of beneficial pulmonary vascular remodelling, which can be helpful for evaluating a PAH patient. Consequently, measuring the hemodynamic response to a vasodilator, for example inhaled nitric oxide, may indicate possible pulmonary vascular remodelling. The measurement can then be used to support a change in patient management for carefully selected patients, for instance, in support of transitioning a patient from prostanoid therapy to alternative therapies. Ultimately, this information may result in individual patient management strategies that pose less risk, improve quality of life, and cost less, thus imparting a positive effect on clinical outcome.

Inhaled nitric oxide (NO) can be administered during right heart catheterization (RHC) to evaluate and characterize pulmonary hemodynamics following long term parenteral prostacyclin therapy and can provide information that may influence the choice of treatment strategies for these patients. These treatment strategies may involve changing vasodilator therapy, eligibility for lung and/or heart transplantation, or changes in prognosis. Inhaled nitric oxide can be a potent, selective pulmonary vasodilator agent and has been well studied up to 80 ppm. It is expected that inhaled nitric oxide as a diagnostic agent during RHC may be useful for facilitating patient management strategies and provide clinical information beneficial to patient care.

In sum, despite the promising reports of successful transition from continuous infusion therapy, patient selection and factors that may predict success remain unclear. Therefore, there remains a need for methods of evaluating PAH patients, patients who are undergoing parenteral prostacyclin therapy, and patients who are candidates for transitioning from parenteral prostacyclin therapy to an alternative therapy.

Transition of Patients from Prostanoid Therapy

Pulmonary arterial hypertension (PAH) is a rare disease of the pulmonary vessels that currently has no cure. PAH can eventually affect the right ventricle (RV). Right ventricular performance can be key in explaining symptoms, pathophysiology, and survival in PAH. At least one report has that ~70% of PAH deaths can be attributed to RV failure. (D'Alonzo, et al., 1991). Current therapies can remain palliative, improving symptoms, hemodynamics and longevity, while morbidity and mortality in this population can remain very high.

Several case studies have reported the successful wean from epoprostenol, a prostacyclin, to oral agents. (Kim, et al., 2003; Johnson, et al., 2007). These studies have also demonstrated normalization of hemodynamics, with two reported cases where patient's exhibited return of vasoreactivity after treatment with epoprostenol. A search of the literature revealed 63 reports of experiences with the transition of patients from prostanoid therapy which shared the following common criteria: 1) normalization/stable hemodynamics, 2) stable dose of prostanoid therapy, 3) stable Functional Class and 4) no clinical signs of heart failure, (JVD, edema, etc.).

Among these experiences there are instances where pulmonary hemodynamics had improved. This may support a theory that some degree of positive remodeling occurs, possibly more frequently than initially thought. The same trend was noted in the data review of the MUST study, although the positive remodeling phenomenon alone does not seem to be a reliable characteristic to determine the success or failure of the wean/transition process.

Reports of improved hemodynamics can be found in the literature, which can support the positive effect of epoprostenol, as in the instance of Barst, et al. (1996). This is of particular interest because the findings correlated with the results of a six mile walk test (6MWD), as well. This study, a 12-week open-label, prospective, randomized, multicenter study of 81 patients in which the active group, (n=41) demonstrated an improvement in hemodynamics treatment with average decline of 8% in the mean pulmonary arterial pressure and a 21% decline in pulmonary vascular resistance.

McLaughlin, et al. (1998) reported similar findings with an improvement in symptoms, hemodynamic measures and a reduction in pulmonary vascular resistance with epoprostenol therapy in a prospective study of 27 consecutive patients. Twenty-six of the 27 patients demonstrated signs of overall improvement, where pulmonary vascular resistance declined by 53%, cardiac output increased by 67%, and mean pulmonary artery pressure declined 22%.

Despite these findings, the improved clinical outcomes for this population and the availability of several pulmonary-specific vasodilators, the median survival for patients with no treatment can be 2.8 years with 1-, 3-, and 5-year survival rates of 68%, 48%, and 34%, respectively. Continuous prostanoid therapy may have improved median survival at 1-, 3-, and 5-years 97-99%, 63-71% and 56%, respectively. (McLaughlin, 2002 et al., Barst, 2006, et al.). Right ventricular (RV) dysfunction can be the main cause of death in this population and has been estimated to be responsible for at least 70% of all PAH deaths.

Right Ventricle

Normally, the right ventricle (RV) can perform against very little resistance, can be a thin walled compliant chamber. The RV can be more adaptive to sudden increases in volume and can be less tolerant to sudden increases in afterload. Capable of maintaining a relatively stable cardiac output, the RV can accommodate significant variations in volume but can be poorly adapted to generating high pressure, particularly in situations where there is a sudden increase in afterload. A sudden increase in afterload can follow massive pulmonary emboli.

In pulmonary hypertension, RV dysfunction and failure can be the result of the increased longstanding pressure overload of the RV. It may not be the degree of pulmonary hypertension (pulmonary artery pressure) that correlates with symptoms or survival, but RV mass, RV size and/or right atrial pressure that can reflect functional status and can be strong predictors of survival. (Voelkel, et al., 2006). In the PAH population, the 6-minute walk test (6MWT or 6MWD) can be used as a measure of outcome and can correlate better with RV function than pulmonary artery pressure. (ATS Committee on Proficiency Standards for Clinical Pulmonary Function Laboratories, "ATS Statement: Guidelines for the Six-Minute Walk Test," Am J Respir Crit. Care Med, Vol. 166, pp. 111-117, 2002, which incorporated by reference in its entirety). However, the 6-minute walk test may not provide information on RV-pulmonary vascular function.

In PAH, the increase in afterload can manifest as elevated pulmonary vascular resistance. The RV can initially adapt to the increased pressure with myocardial hypertrophy minimizing wall stress through Laplace Law. This initial compensation can lead to eventual decompensation, chamber dilatation, heart failure and/or left ventricular diastolic dysfunction. Abnormal RV function can be reversed with effective medical therapy as can be seen with stabilization and improved exercise capacity. (Hinderliter et al., 1997).

Prostacyclin therapy can be intended to target the pulmonary vascular bed, by decreasing pulmonary pressures. Therapy can be implemented at very low doses of prostacyclin and continually up-titrated to achieve the established target dose or until dose limiting side effects occur. The idea that continuous up-titration, regardless of clinical status, can be required is under question. Continuous up-titration can lead to excessively high cardiac output and even high output heart failure. A better option may be to conduct frequent reassessment of symptoms, exercise capacity and periodic hemodynamic evaluations.

Prostacyclin therapies can restore the vasodilator/vasoconstrictor balance and can improve pulmonary hemodynamics, exercise capacity and/or survival. However, this complicated therapy may not be without its own associated risks, and in many instances, the opportunity to transition to alternative less complicated therapies can also have risks. Rapid deterioration with no response to resumption of prostacyclin therapy can occur.

Criteria for the selection of patients that may be considered suitable for wean or transition can include two recommendations for patient selection: 1) stable/normalization of hemodynamics and/or 2) no clinical evidence of heart failure (Table 1). There may be support that, following prostacyclin therapy, pulmonary pressure can improve and pulmonary vascular resistance (PVR) can decrease.

The second of the common patient selection criteria, clinical evidence of heart failure, has previously been evaluated during clinical assessment for the presence of jugular vein distension (JVD), peripheral edema and presence of a third heart sound at the time of wean. The echocardiography data available did not seem to correlate reliably with the clinical presentation. Some cases presented did have clinical documentation of signs of heart failure, but the ECHO was not supportive of these findings. No recent catheterization data found supports the clinical findings, which may give credence to assessing RV systolic function.

The increase in PVR can lead to increased RV afterload. The fixed nature of this pressure overload may restrict the ability of the RV to augment cardiac output (CO). Cardiac catheterization can be the gold standard for the diagnosis and management of PH and RV dysfunction. However, it can provide the only direct measurement of right sided pressures and direct measurement of RV afterload, disease severity and determining prognostic markers (RAP, CO and mPAP). (Alonzo et al., 1991).

The characterization of stable hemodynamics and RV function can provide an indication of the effect of afterload reduction and the RV-pulmonary vascular relationship following long term treatment. This can help to guide and optimize patient management. In the presence of normal RV function and pulmonary hypertension, there can be minimal influence on RV ejection fraction or cardiac output (Bhorade, 1999, et al.). Identification of the RV-pulmonary vascular relationship may also allow for the detection and progression of arteriopathy and the subsequent decline of RV function earlier than current diagnostic methods.

Vasodilator challenge following therapy, particularly parenteral prostacyclin therapy, can be useful as a diagnostic agent. For example, vasodilator challenge can provide information to guide medical management. Following inhalation of nitric oxide, a reduction in PVR can allow for assessment of the RV hemodynamic response, the assessment of RV function and/or the inotropic effect of prostacyclin therapy. The information obtained from a vasodilator challenge can aid in the determination of the stability of hemodynamics, the RV-pulmonary vascular response to afterload reduction, the preservation of RV function.

Repeat vasoreactivity testing (i.e. vasodilator challenge) can be a method suitable for the identification and optimization of PAH therapy (e.g. medication adjustments) and/or characterization of the RV and response to a reduction in afterload. This information can provide significant clinical information regarding the RV-pulmonary vascular relationship. Right ventricular function can be determined and a measure of outcomes information regarding the function of the RV can aid in early detection of heart failure and consequently failure to transition from a parental prostacyclin. Therefore, right ventricular function can guide treatment decisions and the optimization of patient management.

Study Results

Objectives/Hypothesis

An aim of the project was to collect and review the existing data from centers experienced with the practice of transition from parenteral prostacyclins to an alternative therapy. The review was conducted to determine if a population could be characterized based on the hemodynamic response using inhaled nitric oxide during right heart catheterization. A primary objective of the project was to determine the correlation, if any, between the return of pulmonary vascular reactivity following parenteral prostacyclin therapy and the ability of the patient to transition from parenteral prostacyclins to an alternative therapy. Secondary objectives included the exploration of clinical characteristics of a patient population with a documented wean or transition from parenteral prostacyclins, as well as evaluating any change in clinical impression.

Method

To date seven sites have contributed to the data set collected for a total of 47 baseline visits, and 246 follow-up visits. There are five failed weans and seven late failures. Data was available to review for 40 cases entered. No statistical analysis was performed and reviews completed were descriptive in order to identify any shared characteristics in the population either as a success, failure or late failure.

Due to the retrospective nature of the study, the data sets collected for each case at baseline through follow-up are not complete and statistical interpretation is limited. However, the summary review of the data entered for the MUST Study, in addition to the reported cases in the literature identifying experiences with successful transition from parenteral prostanoid, may provide a sufficient amount of information that will guide the pivotal Phase 3 study in this development program.

This data reviewed collectively with published literature has identified a link between the return of a degree of vasoreactivity and the suitability for wean or transition from parenteral prostacyclin therapy and the characterization of the population that have a reported wean/transition.

Three cases, where nitric oxide re-challenge data was available at the time of subject wean, are represented in Table 2.

TABLE 2

Nitric oxide challenge at time of wean

| PAPm | NO PAPm | CO | NO CO | PVR | NO PVR | IV Prost |
|---|---|---|---|---|---|---|
| 45 | 49 | 3.7 | 5.2 | 10 | 8.3 | Yes |
| 54 | 48 | 7.3 | 7.8 | 10.2 | 3.8 | No |
| 75 | 70 | 4.77 | 4.77 | 14.6 | 14.4 | No |

As can be seen, there was only a modest decrease in the PAPm for all three cases. The modest decreases failed to meet the criteria of acute vasodilator response, defined as a fall in PAPm of >10 mm Hg to <40 mm Hg. Of interest was the effect of inhaled nitric oxide in the case of the failed transition, a marked increase in the CO and a minimal decrease in PVR suggested the RV compliance had been affected because the increase in CO did not correlate with the decrease in PVR. Review of the five failure to wean cases and four of the seven late failures showed the presence of right ventricular enlargement in four of the five failure to wean cases (with one blank) and in three of the four reviewed late failure cases. In these cases, the clinical findings did not correlate with the ECHO data.

The lack of correlation between the clinical findings and the ECHO data prompted review of the data. Baseline hemodynamics, wean hemodynamics and echocardiography data were reviewed for all the failed transitions. Table 3 provides a summary of the available data. A trend was noted among the cases that failed to wean or were identified as late failures having to return to prostacyclin therapy. In each case, where echocardiography data was available and right ventricular enlargement was indicated and/or right ventricular dysfunction was indicated, a failed wean or late failure was common. This data was not considered conclusive due to the small sample size and missing data.

In one aspect, a method for treating pulmonary arterial hypertension in a patient can include determining whether a patient with pulmonary arterial hypertension has an enlarged right ventricle or right ventricular dysfunction.

In some embodiments, the patient has previously been administered a prostanoid. A prostanoid can include a prostaglandin, a prostaglandin derivative or a thromboxane. A prostanoid can include prostacyclin, epoprostenol, treprostinil, iloprost orberaprost. A prostanoid can be administered intravenously, subcutaneously, orally (e.g. liquid, tablet or capsule) or by inhalation. A patient can be administered a prostanoid as part of a treatment course. A course can include administration of the prostanoid at least once a day, at least once a week or at least once a month. A course can

TABLE 3

Hemodynamics Failures

| Baseline-Time of Diagnosis | | | | | | Time of Wean | | | | | | | |
|---|---|---|---|---|---|---|---|---|---|---|---|---|---|
| BL PAPm | BL NO PAPm | BL CO | BL NO CO | BL PVR | BL NO PVR | WN PAPm | WN NO PAPm | WN CO | WN NO CO | WN PVR | WN NO PVR | IV Prost | Prost Date |
| 60 |  | 3.77 |  | 13 |  | 34 |  | 5.74 |  | 3.8 |  | Yes | Mar. 14, 2005 |
| 37 | 32 | 2.31 | 2.86 | 6.5 | 3.2 | 26 |  | 2.91 |  | 5.2 |  | Yes | No wean |
| 53 | 42 | 4.2 | 4.4 | 9.2 | 6 | 49 |  | 5.8 |  | 6.3 |  | Yes | No wean |
| 58 | 56 | 5.8 | 5.8 | 8 | 7.2 | 47 |  | 8.53 |  | 3.9 |  | Yes | No wean |
| 56 | 52 | 4.3 | 6.5 | 6.98 | 6.3 | 52 |  | 5.49 |  | 7.84 |  | Yes | No wean |
| 72 |  | 4.24 |  | 12.5 |  | 46 |  | 5.47 |  | 7.25 |  | Yes | No wean |
| 34 | 35 | 5.2 | 5.6 | 5.77 | 4.49 |  |  |  |  |  | Exp. | Yes | May 22, 2003 |
| 70 | 61 | 4.28 | 5.15 | 13.1 |  |  |  |  |  |  | Exp. | Yes | Jul. 23, 2001 |
| 46 | 48 | 3.6 | 5.3 | 10.3 | 7.7 | 45 | 49 | 3.7 | 5.2 | 10 | 8.3 | Yes | Apr. 4, 2005 |
| 51 | 61 | 5.4 | 7 |  |  |  |  |  |  |  |  | Yes | Aug. 7, 2007 |
| 50 | 50 | 3.5 | 4.2 | 10.9 | 9 |  |  |  |  |  |  | Yes | Jul. 5, 2002 |
|  |  |  |  |  |  | 32 |  | 3.76 |  | 6.38 |  | Yes | Jan. 1, 1997 |

TABLE 4

Hemodynamics Success

| Baseline-Time of Diagnosis | | | | | | Time of Wean | | | | | | |
|---|---|---|---|---|---|---|---|---|---|---|---|---|
| BL PAPm | BL NO PAPm | BL CO | BL NO CO | BL PVR | BL NO PVR | WN PAPm | WN NO PAPm | WN CO | WN NO CO | WN PVR | WN NO PVR | IV Prost |
| 54 | 40 | 3 | 4.02 | 13.3 | 5.97 | 26 |  | 7.14 |  | 3.2 |  | No |
| 51 |  |  |  |  |  | 18 |  | 8.8 |  | 1.1 |  | No |
| 57 |  | 1.9 |  | 27.4 |  | 30 |  | 3.92 |  | 5.6 |  | No |
| 60 |  | 2.4 |  | 19.2 |  | 36 |  | 5.37 |  | 5.4 |  | No |
| 46 |  | 3.1 |  | 4.5 |  | 45 |  | 5.9 |  | 6.27 |  | No |
|  |  |  |  |  |  | 37 |  | 5.62 |  | 4.2 |  | No |
| 43 | 40 | 4.9 | 4.8 | 7.55 | 6.66 |  |  | 6.9 |  | 1.87 |  | No |
| 40 |  | 2.1 |  | 11.18 |  | 15 |  | 5.86 |  | 0.85 |  | No |
| 33 | 26 | 4.71 | 5.4 | 5.7 | 3.41 | 32 |  | 4.09 |  | 6.6 |  | No |
| 51 |  | 6.2 |  | 6.4 |  | 53 |  | 5.7 |  | 7.6 |  | No |
| 57 |  | 6.4 |  | 12 |  | 85 |  | 4.05 |  | 20 |  | No |
| 59 | 50 | 5.7 | 7.2 | 9.5 | 6.3 | 61 |  | 4.76 |  | 11.5 |  | No |
| 90 |  | 6.8 |  | 12.1 |  | 72 |  | 7.63 |  | 7.9 |  | No |
| 42 |  |  |  | 7.71 |  | 37 | 41 | 6.55 |  | 4.58 | 3.11 | No |
| 58 |  | 58 |  | 2.5 |  | 4.1 |  | 18 |  |  |  | No |
| 58 | 52 | 4.5 | 4.2 | 16.48 | 10.7 | 54 | 48 | 7.3 | 7.8 | 10.2 | 3.8 | No |
| 75 | 70 | 4.77 | 4.77 | 14.6 | 14.4 | 75 | 70 | 4.77 | 4.77 | 14.6 | 14.4 | No |

Vasoreactive Methods

Therefore, in one aspect, a method can include vasoreactivity testing to provide a medical professional with information regarding the status of a patient with a pulmonary condition.

last for at least three months, at least six months, at least one year, at least two years, or more than two years.

In some embodiments, a patient can be a neonate (i.e. less than one month old), an infant (at least one month to one year old) or a toddler (at least one year to three years old).

In other embodiments, a patient can be a child (at least three years to 18 years old). More specifically, a patient can be a young child (at least three years to seven years old). In still other embodiments, a patient can be an adult (at least 18 years old).

In some embodiments, determining if the patient has an enlarged right ventricle or right ventricular dysfunction can include administering a vasoactive agent to the patient. A vasoactive agent can cause vasculature to dilate, increasing the internal diameter of the vasculature. In some embodiments, a vasoactive agent can be inhaled nitric oxide.

In some embodiments, administering inhaled nitric oxide can include communicating an air flow including nitrogen dioxide through a receptacle. The receptacle can include an inlet, an outlet, and/or a surface-active material.

In some embodiments, a surface-active material can include a reducing agent. Any appropriate reducing agent that can convert $NO_2$ or $N_2O_4$ to NO can be used as determined by a person of skill in the art. For example, a reducing agent can include a hydroquinone, glutathione, thiols, nitrites, and/or one or more reduced metal salts such as Fe(II), Mo(VI), NaI, Ti(III) or Cr(III). A reducing agent can be an antioxidant. An antioxidant can be an aqueous solution of an antioxidant. An antioxidant can be ascorbic acid, alpha tocopherol, or gamma tocopherol. Any appropriate antioxidant can be used depending on the activities and properties as determined by a person of skill in the art. An antioxidant can be used dry or wet. A surface-active material can be coated with a reducing agent or coated with an aqueous solution of a reducing agent.

In some embodiments an inlet can be configured to receive the flow of nitrogen dioxide.

In some embodiments, administering nitric oxide can include communicating the air flow to the outlet through the surface-active material.

In some embodiments, administering nitric oxide can include converting the gaseous nitrogen dioxide to nitric oxide, most preferably, at ambient temperature.

In some embodiments, a vasoactive agent can be administered repeatedly. In some embodiments, a vasoactive agent can be administered at least twice, at least three times, at least four times, at least five times, at least ten times or greater than ten times.

In some embodiments, determining whether the patient has an enlarged right ventricle or right ventricular dysfunction can include monitoring an at least one indicator of hemodynamics of the patient. Monitoring at least one indicator can include measuring a hemodynamic property. For example, a hemodynamic property or an at least one indicator can include pulmonary vascular resistance, mean pulmonary arterial pressure or cardiac output. Hemodynamics can be anything relating to the movement, flow or circulation of blood. An indicator of hemodynamics can include, but is not limited to, a pressure, a volume or a rate.

Monitoring an at least one indicator can include monitoring at any time point during a method. In some embodiments, monitoring can include monitoring the at least one indicator of the hemodynamics of the patient before administering a vasoactive agent to the patient. In some embodiments, monitoring can include monitoring the at least one indicator of the hemodynamics of the patient after administering a vasoactive agent to the patient.

In some embodiments, determining whether the patient has an enlarged right ventricle or right ventricular dysfunction can include calculating a change in at least one indicator of the hemodynamics of the patient between before the inhaled nitric oxide was administered and after the inhaled nitric oxide was administered. For example, an at least one indicator of the hemodynamics of the patient can be monitored before administration of a vasoactive agent and then the at least one indicator of the hemodynamics of the patient can be monitored after administration of a vasoactive agent. The difference between the indicator of the hemodynamics of the patient can be determined or calculated based on at least those two time points. A change in at least one indicator of the hemodynamics of the patient can be a negative value, zero or a positive value.

In some embodiments, the at least one indicator of hemodynamics can include pulmonary vascular resistance and cardiac output. In some embodiments, determining whether the patient has an enlarged right ventricle or right ventricular dysfunction can include determining the presence of an increase in cardiac output after administration of nitric oxide which correlates with a decrease in pulmonary vascular resistance after administration of nitric oxide. For example, a minimal decrease in pulmonary vascular resistance can correlate with a minimal increase in cardiac output. Accordingly, a moderate decrease in pulmonary vascular resistance can correlate with a moderate increase in cardiac output, and a marked decrease in pulmonary vascular resistance can correlate with a marked increase in cardiac output. A minimal decrease in pulmonary vascular resistance can be a decrease of at least zero mmHg·min/l and at most 0.2 mmHg·min/l, a moderate decrease in pulmonary vascular resistance can be a decrease of at least 0.2 mmHg·min/l and at most 1.0 mmHg·min/l, and a marked decrease can be of at least 1.0 mmHg·min/l. A pulmonary vascular resistance can also increase. A minimal increase in cardiac output can be at least 0.0 l/min to at most 0.1 l/min, a moderate increase in cardiac output can be at least 0.1 l/min to at most 0.3 l/min, a marked increase in cardiac output can be at least 0.3 l/min. Also, cardiac output can decrease.

In some embodiments, a decrease of at least 0.2 mmHg·min/l in pulmonary vascular resistance can correlate with an increase of at least 0.1 l/min in cardiac output.

In some embodiments, a statistically significant decrease in pulmonary vascular resistance can correlate with a statistically significant increase in cardiac output. Statistical significance can be independent of the magnitude of change (i.e. minimal, moderate, marked). Statistical significance can be determined using any of a variety of statistical tests known to those of skill in the art, including but not limited to, chi-square test, student's t-test, z-test, Fisher's exact test, runs test, Kolmogorov-Smirnov test, Mann-Whitney U test, Wald-Wolfowitz runs, Kruskal-Wallis test, Jonckheere-Terpstra test, McNemar test, Wilcoxon sign test, Friedman test, Kendall's W test and Cochran Q test.

In some embodiments, an increase in cardiac output which correlates with a decrease in pulmonary vascular resistance can indicate that an enlarged right ventricle or right ventricular dysfunction may not be present. A decrease in pulmonary vascular resistance can occur as a result of vasodilation. Therefore, as pulmonary vascular resistance decreases, a correlative increase in cardiac output can be expected, particularly when the right ventricle is functioning properly. On the other hand, a decrease in pulmonary vascular resistance without a correlative cardiac output can indicate that the right ventricle is unable to respond in the change in the hemodynamics and can suggest an enlarged right ventricle or right ventricular dysfunction.

In some embodiments, the method can include weaning the patient off of the prostanoid if the patient does not have an enlarged right ventricle or right ventricular dysfunction. Weaning can mean the decreasing the amount of prostanoid administered over time to a patient during a given unit of time (e.g. per day, per week, per month), most preferably, decreasing the amount to zero.

In another aspect, a method for treating pulmonary arterial hypertension in a patient can include administering a vasoactive agent to a patient with pulmonary arterial hypertension. The patient may have previously been administered a prostanoid. A prostanoid can include a prostaglandin, a prostaglandin derivative or a thromboxane. A prostanoid can include prostacyclin, epoprostenol, trepostinil, iloprost orberaprost. A prostanoid can be administered intravenously, subcutaneously, orally (e.g. liquid, tablet or capsule) or by inhalation. A patient can be administered a prostanoid as part of a treatment course. A course can include administration of the prostanoid at least once a day, at least once a week or at least once a month. A course can last for at least three months, at least six months, at least one year, at least two years, or more than two years.

In some embodiments, a patient can be a neonate (i.e. less than one month old), an infant (at least one month to one year old) or a toddler (at least one year to three years old). In other embodiments, a patient can be a child (at least three years to 18 years old). More specifically, a patient can be a young child (at least three years to seven years old). In still other embodiments, a patient can be an adult (at least 18 years old).

In some embodiments, a method can include determining whether the patient demonstrates an acute vasodilator response to the vasoactive agent. A vasoactive agent can cause vasculature to dilate, increasing the internal diameter of the vasculature. In some embodiments, a vasoactive agent can be inhaled nitric oxide.

In some embodiments, administering inhaled nitric oxide can include communicating an air flow including nitrogen dioxide through a receptacle. The receptacle can include an inlet, an outlet, and/or a surface-active material.

In some embodiments, a surface-active material can include a reducing agent. Any appropriate reducing agent that can convert $NO_2$ or $N_2O_4$ to NO can be used as determined by a person of skill in the art. For example, a reducing agent can include a hydroquinone, glutathione, thiols, nitrites, and/or one or more reduced metal salts such as Fe(II), Mo(VI), NaI, Ti(III) or Cr(III). A reducing agent can be an antioxidant. An antioxidant can be an aqueous solution of an antioxidant. A antioxidant can be ascorbic acid, alpha tocopherol, or gamma tocopherol. Any appropriate antioxidant can be used depending on the activities and properties as determined by a person of skill in the art. An antioxidant can be used dry or wet. A surface-active material can be coated with a reducing agent or coated with an aqueous solution of a reducing agent.

In some embodiments an inlet can be configured to receive the flow of nitrogen dioxide.

In some embodiments, administering nitric oxide can include communicating the air flow to the outlet through the surface-active material.

In some embodiments, administering nitric oxide can include converting the gaseous nitrogen dioxide to nitric oxide, most preferably, at ambient temperature.

In some embodiments, a vasoactive agent can be administered repeatedly. In some embodiments, a vasoactive agent can be administered at least twice, at least three times, at least four times, at least five times, at least ten times or greater than ten times.

In some embodiments, determining whether the patient demonstrates an acute vasodilator response to the vasoactive agent can include monitoring an at least one indicator of hemodynamics of the patient. Monitoring at least one indicator can include measuring a hemodynamic property. For example, a hemodynamic property or an at least one indicator can include pulmonary vascular resistance, mean pulmonary arterial pressure or cardiac output. Hemodynamics can be anything relating to the movement, flow or circulation of blood. An indicator of hemodynamics can include, but is not limited to, a pressure, a volume or a rate.

Monitoring an at least one indicator can include monitoring at any time point during a method. In some embodiments, monitoring can include monitoring the at least one indicator of the hemodynamics of the patient before administering a vasoactive agent to the patient. In some embodiments, monitoring can include monitoring the at least one indicator of the hemodynamics of the patient after administering a vasoactive agent to the patient.

In some embodiments, determining whether the patient demonstrates an acute vasodilator response to the vasoactive agent can include calculating a change in at least one indicator of the hemodynamics of the patient between before the vasoactive was administered and after the vasoactive was administered. For example, an at least one indicator of the hemodynamics of the patient can be monitored before administration of a vasoactive agent and then the at least one indicator of the hemodynamics of the patient can be monitored after administration of a vasoactive agent. The difference between the indicator of the hemodynamics of the patient can be determined or calculated based on at least those two time points. A change in at least one indicator of the hemodynamics of the patient can be a negative value, zero or a positive value.

In some embodiments, the at least one indicator of hemodynamics can include mean pulmonary arterial pressure. In some embodiments, determining whether the patient demonstrates an acute vasodilator response to the vasoactive agent can include determining the presence of a change in mean pulmonary arterial pressure of greater than 5 mm Hg, greater than 10 mm Hg between, greater than 12 mm Hg or greater than 15 mm Hg before the inhaled nitric oxide was administered and after the inhaled nitric oxide was administered.

In some embodiments, the method can include weaning the patient off of the prostanoid if the patient demonstrates an acute vasodilator response to the vasoactive agent. Weaning can mean the decreasing the amount of prostanoid administered over time to a patient during a given unit of time (e.g. per day, per week, per month), most preferably, decreasing the amount to zero.

In another aspect, a method for monitoring a patient with pulmonary arterial hypertension can include performing a vasoreactivity challenge test.

In another aspect, a method for monitoring a patient with pulmonary arterial hypertension can include administering inhaled nitric oxide to the patient with pulmonary arterial hypertension.

In some embodiments, a patient can be a neonate (i.e. less than one month old), an infant (at least one month to one year old) or a toddler (at least one year to three years old). In other embodiments, a patient can be a child (at least three years to 18 years old). More specifically, a patient can be a young child (at least three years to seven years old). In still other embodiments, a patient can be an adult (at least 18 years old).

In some embodiments, administering inhaled nitric oxide can include communicating an air flow including nitrogen dioxide through a receptacle. The receptacle can include an inlet, an outlet, and/or a surface-active material.

In some embodiments, a vasoactive agent can be administered repeatedly. In some embodiments, a vasoactive agent can be administered at least twice, at least three times, at least four times, at least five times, at least ten times or greater than ten times.

In some embodiments, a surface-active material can include a reducing agent. Any appropriate reducing agent that can convert $NO_2$ or $N_2O_4$ to NO can be used as determined by a person of skill in the art. For example, a reducing agent can include a hydroquinone, glutathione, thiols, nitrites, and/or one or more reduced metal salts such as Fe(II), Mo(VI), NaI, Ti(III) or Cr(III). A reducing agent can be an antioxidant. An antioxidant can be an aqueous solution of an antioxidant. A antioxidant can be ascorbic acid, alpha tocopherol, or gamma tocopherol. Any appropriate antioxidant can be used depending on the activities and properties as determined by a person of skill in the art. An antioxidant can be used dry or wet. A surface-active material can be coated with a reducing agent or coated with an aqueous solution of a reducing agent.

In some embodiments an inlet can be configured to receive the flow of nitrogen dioxide.

In some embodiments, administering nitric oxide can include communicating the air flow to the outlet through the surface-active material.

In some embodiments, administering nitric oxide can include converting the gaseous nitrogen dioxide to nitric oxide, most preferably, at ambient temperature.

In some embodiments, a method can include monitoring an at least one indicator of hemodynamics of the patient. Monitoring at least one indicator can include measuring a hemodynamic property. For example, a hemodynamic property or an at least one indicator can include pulmonary vascular resistance, mean pulmonary arterial pressure or cardiac output. Hemodynamics can be anything relating to the movement, flow or circulation of blood. An indicator of hemodynamics can include, but is not limited to, a pressure, a volume or a rate.

Monitoring an at least one indicator can include monitoring at any time point during a method. In some embodiments, monitoring can include monitoring the at least one indicator of the hemodynamics of the patient before administering inhaled nitric oxide to the patient. In some embodiments, monitoring can include monitoring the at least one indicator of the hemodynamics of the patient after administering inhaled nitric oxide to the patient.

In another aspect, a method for diagnosing right ventricular dysfunction can include administering a vasoactive agent to a patient. A patient can be suspected of having right ventricular dysfunction. A patient can have been diagnosed with pulmonary arterial hypertension.

In some embodiments, a patient can be a neonate (i.e. less than one month old), an infant (at least one month to one year old) or a toddler (at least one year to three years old). In other embodiments, a patient can be a child (at least three years to 18 years old). More specifically, a patient can be a young child (at least three years to seven years old). In still other embodiments, a patient can be an adult (at least 18 years old).

In some embodiments, a vasoactive agent can be administered repeatedly. In some embodiments, a vasoactive agent can be administered at least twice, at least three times, at least four times, at least five times, at least ten times or greater than ten times.

In some embodiments, a vasoactive agent can be nitric oxide, more specifically, inhaled nitric oxide. In some embodiments, administering inhaled nitric oxide can include communicating an air flow including nitrogen dioxide through a receptacle. The receptacle can include an inlet, an outlet, and/or a surface-active material.

In some embodiments, a surface-active material can include a reducing agent. Any appropriate reducing agent that can convert $NO_2$ or $N_2O_4$ to NO can be used as determined by a person of skill in the art. For example, a reducing agent can include a hydroquinone, glutathione, thiols, nitrites, and/or one or more reduced metal salts such as Fe(II), Mo(VI), NaI, Ti(III) or Cr(III). A reducing agent can be an antioxidant. An antioxidant can be an aqueous solution of an antioxidant. A antioxidant can be ascorbic acid, alpha tocopherol, or gamma tocopherol. Any appropriate antioxidant can be used depending on the activities and properties as determined by a person of skill in the art. An antioxidant can be used dry or wet. A surface-active material can be coated with a reducing agent or coated with an aqueous solution of a reducing agent.

In some embodiments an inlet can be configured to receive the flow of nitrogen dioxide.

In some embodiments, administering nitric oxide can include communicating the air flow to the outlet through the surface-active material.

In some embodiments, administering nitric oxide can include converting the gaseous nitrogen dioxide to nitric oxide, most preferably, at ambient temperature.

In some embodiments, a method can include monitoring an at least one indicator of hemodynamics of the patient. Monitoring at least one indicator can include measuring a hemodynamic property. For example, a hemodynamic property or an at least one indicator can include pulmonary vascular resistance, mean pulmonary arterial pressure or cardiac output. Hemodynamics can be anything relating to the movement, flow or circulation of blood. An indicator of hemodynamics can include, but is not limited to, a pressure, a volume or a rate.

Monitoring an at least one indicator can include monitoring at any time point during a method. In some embodiments, monitoring can include monitoring the at least one indicator of the hemodynamics of the patient before administering a vasoactive agent to the patient. In some embodiments, monitoring can include monitoring the at least one indicator of the hemodynamics of the patient after administering a vasoactive agent to the patient.

In some embodiments, a method can include determining whether the patient has right ventricular dysfunction.

In some embodiments, the at least one indicator of hemodynamics can include pulmonary vascular resistance and cardiac output. In some embodiments, determining whether the patient has right ventricular dysfunction can include determining the presence of an increase in cardiac output after administration of nitric oxide which correlates with a decrease in pulmonary vascular resistance after administration of nitric oxide. For example, a minimal decrease in pulmonary vascular resistance can correlate with a minimal increase in cardiac output. Accordingly, a moderate decrease in pulmonary vascular resistance can correlate with a moderate increase in cardiac output, and a marked decrease in pulmonary vascular resistance can correlate with a marked increase in cardiac output. A minimal decrease in pulmonary vascular resistance can be a decrease of at least zero mmHg·min/l and at most 0.2 mmHg·min/l, a moderate decrease in pulmonary vascular resistance can be a decrease of at least 0.2 mmHg·min/l and at most 1.0 mmHg·min/l, and a marked decrease can be of at least 1.0 mmHg·min/l. A pulmonary vascular resistance can also increase. A minimal increase in cardiac output can be at least 0.0 l/min to at most 0.1 l/min, a moderate increase in cardiac output can be at least 0.1 l/min to at most 0.3 l/min, a marked increase in cardiac output can be at least 0.3 l/min. Also, cardiac output can decrease.

In some embodiments, a decrease of at least 0.2 mmHg·min/l in pulmonary vascular resistance can correlate with an increase of at least 0.1 l/min in cardiac output.

In some embodiments, a statistically significant decrease in pulmonary vascular resistance can correlate with a statistically significant increase in cardiac output. Statistical significance can be independent of the magnitude of change (i.e. minimal, moderate, marked). Statistical significance can be determined using any of a variety of statistical tests known to those of skill in the art, including but not limited to, chi-square test, student's t-test, z-test, Fisher's exact test, runs test, Kolmogorov-Smirnov test, Mann-Whitney U test, Wald-Wolfowitz runs, Kruskal-Wallis test, Jonckheere-Terpstra test, McNemar test, Wilcoxon sign test, Friedman test, Kendall's W test and Cochran Q test.

In some embodiments, an increase in cardiac output which correlates with a decrease in pulmonary vascular resistance can indicate that an enlarged right ventricle or right ventricular dysfunction may not be present. A decrease in pulmonary vascular resistance can occur as a result of vasodilation. Therefore, as pulmonary vascular resistance decreases, a correlative increase in cardiac output can be expected, particularly when the right ventricle is functioning properly. On the other hand, a decrease in pulmonary vascular resistance without a correlative cardiac output can indicate that the right ventricle is unable to respond in the change in the hemodynamics and can suggest an enlarged right ventricle or right ventricular dysfunction.

Regardless of the method, in some embodiments, a vasoactive agent can include nitric oxide, most preferably, inhaled nitric oxide. When delivering nitric oxide (NO) for therapeutic use to a mammal, it can be important to avoid delivery of nitrogen dioxide ($NO_2$) to the mammal. Nitrogen dioxide ($NO_2$) can be formed by the oxidation of nitric oxide (NO) with oxygen ($O_2$). The rate of formation of nitrogen dioxide ($NO_2$) can be proportional to the oxygen ($O_2$) concentration multiplied by the square of the nitric oxide (NO) concentration.

A NO delivery system can convert nitrogen dioxide to nitric oxide. A NO delivery system can include a surface-active material. A surface-active material can include a reducing agent. Any appropriate reducing agent that can convert $NO_2$ or $N_2O_4$ to NO can be used as determined by a person of skill in the art. For example, a reducing agent can include a hydroquinone, glutathione, thiols, nitrites, and/or one or more reduced metal salts such as Fe(II), Mo(VI), NaI, Ti(III) or Cr(III). A reducing agent can be an antioxidant. An antioxidant can be an aqueous solution of an antioxidant. A antioxidant can be ascorbic acid, alpha tocopherol, or gamma tocopherol. Any appropriate antioxidant can be used depending on the activities and properties as determined by a person of skill in the art. An antioxidant can be used dry or wet. A surface-active material can be coated with a reducing agent or coated with an aqueous solution of a reducing agent.

The system can employ a surface-active material coated with a reducing agent, for example an antioxidant, as a simple and effective mechanism for making the conversion. More particularly, $NO_2$ can be converted to NO by passing the dilute gaseous $NO_2$ over a surface-active material including a reducing agent, e.g. an antioxidant, such that the reducing agent reacts with the $NO_2$. As an example, when the aqueous antioxidant is ascorbic acid (that is, vitamin C), the reaction can be quantitative at ambient temperatures.

One example of a surface-active material can be silica gel. Another example of a surface-active material that can be used is cotton. The surface-active material may be or may include a substrate capable of retaining a liquid, for example, water. A surface-active material can include a relatively large surface area. A surface-active material can also allow a fluid to pass through it. Another type of surface-active material that has a large surface area that is capable of absorbing moisture also may be used.

FIG. 1 illustrates a cartridge 100 for generating NO by converting $NO_2$ to NO. The cartridge 100, which may be referred to as a cartridge, a converter, a NO generation cartridge, a GENO cartridge, or a GENO cylinder or Nitrosyl™ Primary Cartridge, can include an inlet 105 and an outlet 110. Screen and/or glass wool 115 can be located at the inlet 105 and/or the outlet 110. The remainder of the cartridge 100 can be filled with a surface-active material 120 that is coated with a reducing agent. The surface-active material can be soaked with a saturated solution including a reducing agent to coat the surface-active material. The saturated solution can be, for example, an antioxidant in water. The screen and/or glass wool 115 can also be soaked with the saturated solution before being inserted into the cartridge 100. The antioxidant can be ascorbic acid.

In a general process for converting $NO_2$ to NO, a gas flow (e.g. air flow) having $NO_2$ can be received through the inlet 105. The gas flow can be fluidly communicated to the outlet 110 through the surface-active material 120 coated with the aqueous reducing agent, e.g. antioxidant. As long as the surface-active material remains moist and the reducing agent may not been used up in the conversion, the general process can be effective at converting $NO_2$ to NO at ambient temperature.

The inlet 105 also may receive a gas flow, e.g. air flow, having $NO_2$, for example, from source of $NO_2$. A source of $NO_2$ can include a pressurized bottle of $NO_2$, which also may be referred to as a tank of $NO_2$. The inlet 105 also may receive a gas flow with $NO_2$ in nitrogen ($N_2$), air, or oxygen ($O_2$). The conversion can occur over a wide concentration range. Experiments have been carried out at concentrations in a gas including from about 2 ppm $NO_2$ to 100 ppm $NO_2$, and even to over 1000 ppm $NO_2$. In one example, a cartridge that was approximately 6 inches long and had a diameter of 1.5-inches was packed with silica gel that had first been soaked in a saturated aqueous solution of ascorbic acid. The moist silica gel was prepared using ascorbic acid (i.e., vitamin C) designated as A.C.S reagent grade 99.1% pure from Aldrich Chemical Company and silica gel from Fischer Scientific International, Inc., designated as S8 32-1, 40 of Grade of 35 to 70 sized mesh. Other sizes of silica gel also can be effective. For example, silica gel having an eighth-inch diameter could also work.

The surface active material, e.g. silica gel, can be moistened with a solution including a reducing agent, e.g. a saturated solution including a reducing agent. For example, a saturated solution of ascorbic acid in water; more specifically, the saturated solution can be a saturated solution that had been prepared by mixing 35% by weight ascorbic acid in water, stirring, and straining the water/ascorbic acid mixture through the silica gel, followed by draining. The conversion of $NO_2$ to NO can proceed well when the surface active material (e.g. silica gel) coated with a reducing agent (e.g. ascorbic acid) is moist. The conversion of $NO_2$ to NO may not proceed well with a reducing agent alone, for example, in an aqueous solution of ascorbic acid alone.

The cartridge can be filled with the wet silica gel/reducing agent. For example, a cartridge filled with the wet silica gel/ascorbic acid was able to convert 1000 ppm of $NO_2$ in air to NO at a flow rate of 150 ml per minute, quantitatively, non-stop for over 12 days. A wide variety of flow rates and $NO_2$ concentrations have been successfully tested, ranging from only a few ml per minute to flow rates of up to 5,000 ml per minute. Any appropriate reducing agent that can convert $NO_2$ or $N_2O_4$ to NO can be used as determined by a person of skill in the art. For example, the reducing agent can include a hydroquinone, glutathione, thiols, nitrites, and/or one or more reduced metal salts such as Fe(II), Mo(VI), NaI, Ti(III) or Cr(III). The reducing agent can be an antioxidant. The antioxidant can be an aqueous solution of an antioxidant. The antioxidant can be ascorbic acid, alpha tocopherol, or gamma tocopherol. Any appropriate antioxidant can be used depending on the activities and properties as determined by a person of skill in the art. The antioxidant can be used dry or wet.

The antioxidant/surface-active material GENO cartridge may be used for inhalation therapy. In one such example, the GENO cartridge can be used as a $NO_2$ scrubber for NO inhalation therapy that delivers NO from a pressurized bottle source. The GENO cartridge can be used to remove any $NO_2$ that chemically forms during inhalation therapy. This GENO cartridge can be used to help ensure that no harmful levels of $NO_2$ are inadvertently inhaled by the patient.

The GENO cartridge may be used to supplement or replace some or all of the safety devices used during inhalation therapy in conventional NO inhalation therapy. For example, one type of safety device can warn of the presence of $NO_2$ in air when the concentration of $NO_2$ exceeds a preset or predetermined limit, usually 1 part per million or greater of $NO_2$. Such a safety device may be unnecessary when a GENO cartridge is positioned in a NO delivery system just prior to the patient breathing the NO laden air. The GENO cartridge can convert any $NO_2$ to NO just prior to the patient breathing the NO laden gas, which can make a device to warn of the presence of $NO_2$ in gas unnecessary.

Alternatively or additionally, a $NO_2$ removal cartridge can be inserted just before the attachment of the delivery system to the patient to enhance safety and help ensure that all traces of the toxic $NO_2$ have been removed. The $NO_2$ removal cartridge may be a GENO cartridge used to remove any trace amounts of $NO_2$. Alternatively, the $NO_2$ removal cartridge may include heat-activated alumina. A cartridge with heat-activated alumina, such as supplied by Fisher Scientific International, Inc., designated as A505-212, of 8-14 sized mesh can be effective at removing low levels of $NO_2$ from an air or oxygen stream, and yet can let NO gas pass through without loss. Activated alumina, and other high surface area materials like it, can be used to scrub $NO_2$ from a NO inhalation line.

The various embodiments described are provided by way of illustration only and should not be construed to limit the claimed invention. Those skilled in the art will readily recognize various modifications and changes that may be made to the claimed invention without following the example embodiments and applications illustrated and described herein, and without departing from the true spirit and scope of the claimed invention, which is set forth in the claims.

REFERENCES

1. Barst, R. J., et al. A comparison of continuous intravenous epoprostenol (prostacyclin) with conventional therapy for primary pulmonary hypertension. The Primary Pulmonary Hypertension Study Group. N Engl J Med 334, 296-302 (1996).
2. Barst, R. J., et al Long-term outcome in pulmonary arterial hypertension patients treated with subcutaneous treprostinil. Eur Respir J. 28: 1195-1203 (2006).
3. Barst, R. J., et al. Updated evidence-based treatment algorithm in pulmonary arterial hypertension. J Am Coll Cardiol. 54, S78-84. (2009).
4. Bhorade, S., et al. Response to inhaled nitric oxide in patients with acute right heart syndrome. Am J Respir Crit. Care Med 159, 571-579 (1999).
5. Bloch, K. D., Ichinose, F., Roberts, J. D., Jr. & Zapol, W. M. Inhaled NO as a therapeutic agent. Cardiovasc Res 75, 339-348 (2007).
6. Bogaard, H. J., et al. Chronic Pulmonary Artery Pressure Elevation Is Insufficient to Explain Right Heart Failure. Circulation 120, 1951-1960 (2009).
7. Flox Camacho, Á., et al. Transition From Prostacyclin to Bosentan in Five Patients With Severe Pulmonary Hypertension: The Switch Is Possible. Revista Espariola de Cardiologia 59, 737-739 (2006).
8. Chakinala, M. Changing the Prognosis of Pulmonary Arterail Hypertension: Impact of Medical Therapy. Vol. 26 409-416 (Medscape, 2005).
9. Champion, H. C., Michelakis, E. D. & Hassoun, P. M. Comprehensive Invasive and Noninvasive Approach to the Right Ventricle-Pulmonary Circulation Unit: State of the Art and Clinical and Research Implications. Circulation 120, 992-1007 (2009).
10. Chin, K. M. & Rubin, L. J. Pulmonary arterial hypertension. J Am Coll Cardiol. 51, 1527-1538. (2008).
11. D'Alonzo, G. E., et al. Survival in patients with primary pulmonary hypertension. Results from a national prospective registry. *Ann Intern Med* 115, 343-349 (1991).
12. Di Salvo, T., Mathier, M., Semigran, M. & Dec, G. Preserved right ventricular ejection fraction predicts exercise capacity and survival in advanced heart failure. J Am Coll Cardiol 25, 1143-1153 (1995).
13. Diaz-Guzman, E., Heresi, G. A., Dweik, R. A. & Minai, O. A. Long-term experience after transition from parenteral prostanoids to oral agents in patients with pulmonary hypertension. Respir Med 102, 681-689 (2008).
14. Diller, G.-P., Dimopoulos, K., Kafka, H., Ho, S. Y. & Gatzoulis, M. A. Model of chronic adaptation: right ventricular function in Eisenmenger syndrome. European Heart Journal Supplements 9, H54-H60 (2007).
15. Damman, K., et al. Increased Central Venous Pressure Is Associated With Impaired Renal Function and Mortality in a Broad Spectrum of Patients With Cardiovascular Disease. J Am Coll Cardiol 53, 582-588 (2009).
16. Gaine, S. P. & Rubin, L. J. Primary pulmonary hypertension. *Lancet.* 352, 719-725. (1998).
17. Ghofrani, H. A., Wilkins, M. W. & Rich, S. Uncertainties in the Diagnosis and Treatment of Pulmonary Arterial Hypertension. Circulation 118, 1195-1201 (2008).
18. Gomberg-Maitland, M., et al. Transition from intravenous epoprostenol to intravenous treprostinil in pulmonary hypertension. Am J Respir Crit. Care Med 172, 1586-1589 (2005).
19. Greyson, C. R. Pathophysiology of right ventricular failure. Critical Care Medicine 36, S57-S65 10.1097/1001.CCM.0000296265.0000252518.0000296270 (2008).
20. Haddad, E., Lowson, S. M., Johns, R. A. & Rich, G. F. Use of inhaled nitric oxide perioperatively and in intensive care patients. Anesthesiology 92, 1821-1825 (2000).

21. Haddad, F., Hunt, S. A., Rosenthal, D. N. & Murphy, D. J. Right Ventricular Function in Cardiovascular Disease, Part I: Anatomy, Physiology, Aging, and Functional Assessment of the Right Ventricle. Circulation 117, 1436-1448 (2008).
22. Haddad, F., Doyle, R., Murphy, D. J. & Hunt, S. A. Right Ventricular Function in Cardiovascular Disease, Part II: Pathophysiology, Clinical Importance, and Management of Right Ventricular Failure. Circulation 117, 1717-1731 (2008).
23. Handoko, M. L., et al. Perspectives on novel therapeutic strategies for right heart failure in pulmonary arterial hypertension: lessons from the left heart. European Respiratory Review 19, 72-82 (2010).
24. Hemnes, A. R. & Kawut, S. M. The right ventricle in pulmonary hypertension: from dogma to data. Am J Respir Crit. Care Med 182, 586-588 (2010).
25. Hinderliter, A. L., et al. Effects of Long-term Infusion of Prostacyclin (Epoprostenol) on Echocardiographic Measures of Right Ventricular Structure and Function in Primary Pulmonary Hypertension. Circulation 95, 1479-1486 (1997).
26. Hoeper, M. M., Markevych, I., Spiekerkoetter, E., Welte, T. & Niedermeyer, J. Goal-oriented treatment and combination therapy for pulmonary arterial hypertension. European Respiratory Journal 26, 858-863 (2005).
27. Humbert, M., et al. Survival in patients with idiopathic, familial, and anorexigen-associated pulmonary arterial hypertension in the modern management era. Circulation 122, 156-163 (2010).
28. Inglessis, I., et al. Hemodynamic effects of inhaled nitric oxide in right ventricular myocardial infarction and cardiogenic shock. J Am Coll Cardiol 44, 793-798 (2004).
29. Johnson, R. F., Loyd, J. E., Mullican, A. L., Fink, C. A. & Robbins, I. M. Long-term follow-up after conversion from intravenous epoprostenol to oral therapy with bosentan or sildenafil in 13 patients with pulmonary arterial hypertension. J Heart Lung Transplant 26, 363-369 (2007).
30. Krasuski, R. A., Wang, A., Harrison, J. K., Tapson, V. F. & Bashore, T. M. The response to inhaled nitric oxide in patients with pulmonary artery hypertension is not masked by baseline vasodilator use. Am Heart J 150, 725-728 (2005).
31. Kim, N. H., Channick, R. N. & Rubin, L. J. Successful withdrawal of long-term epoprostenol therapy for pulmonary arterial hypertension. Chest. 124, 1612-1615. (2003).
32. Krasuski, R. A., et al. Inhaled nitric oxide selectively dilates pulmonary vasculature in adult patients with pulmonary hypertension, irrespective of etiology. Journal of the American College of Cardiology 36, p 2204-2211 (2000).
33. Kevin, L. G. & Barnard, M. Right ventricular failure. Continuing Education in Anaesthesia, Critical Care & Pain 7, 89-94 (2007).
34. Lang, I. M. Management of acute and chronic RV dysfunction. European Heart Journal Supplements 9, H61-H67 (2007).
35. Lepore, J. J., et al. Hemodynamic effects of sildenafil in patients with congestive heart failure and pulmonary hypertension: Combined administration with inhaled nitric oxide. Chest 127, 1647-1653 (2005).
36. Leci, E., et al. Prognostic Parameters For Survival Of Patients With Pulmonary Arterial Hypertension Associated To Connective Tissue Diseases Treated With Targeted Therapy. Am. J. Respir. Crit. Care Med. 181, A4844-(2010).
37. Loh, E., Stamler, J. S., Hare, J. M., Loscalzo, J. & Colucci, W. S. Cardiovascular effects of inhaled nitric oxide in patients with left ventricular dysfunction. Circulation. 90, 2780-2785. (1994).
38. Lopez-Candales, A., et al. Right ventricular dyssynchrony in patients with pulmonary hypertension is associated with disease severity and functional class. Cardiovascular Ultrasound 3, 23 (2005).
39. McLaughlin, V. V., Genthner, D. E., Panella, M. M. & Rich, S. Reduction in pulmonary vascular resistance with long-term epoprostenol (prostacyclin) therapy in primary pulmonary hypertension. N Engl J. Med. 338, 273-277. (1998).
40. Moraes, D. L., Colucci, W. S. & Givertz, M. M. Secondary Pulmonary Hypertension in Chronic Heart Failure: The Role of the Endothelium in Pathophysiology and Management. Circulation 102, 1718-1723 (2000).
41. Matthews, J. C., Koelling, T. M., Pagani, F. D. & Aaronson, K. D. The Right Ventricular Failure Risk Score: A Pre-Operative Tool for Assessing the Risk of Right Ventricular Failure in Left Ventricular Assist Device Candidates. J Am Coll Cardiol 51, 2163-2172 (2008).
42. Naeije, R. Pulmonary Hypertension and Right Heart Failure in Chronic Obstructive Pulmonary Disease. Proc Am Thorac Soc 2, 20-22 (2005).
43. Natori, S., et al. Inhaled nitric oxide modifies left ventricular diastolic stress in the presence of vasoactive agents in heart failure. Am J Respir Crit. Care Med 167, 895-901 (2003).
44. Pilcher, D. V., et al. High central venous pressure is associated with prolonged mechanical ventilation and increased mortality after lung transplantation. J Thorac Cardiovasc Surg 129, 912-918 (2005).
45. Price, L. C., Wort, S. J., Finney, S. J., Marino, P. S. & Brett, S. J. Pulmonary vascular and right ventricular dysfunction in adult critical care: current and emerging options for management: a systematic literature review, (2010).
46. Rich, G. F. Management of the Patient with Pulmonary Hypertension and Right Ventricular Failure. ASA Refresher Courses in Anesthesiology 33, 203-212 (2005).
47. Rich, S., et al. The short-term effects of digoxin in patients with right ventricular dysfunction from pulmonary hypertension. Chest 114, 787-792 (1998).
48. Raffy, O., et al. Clinical Significance of the Pulmonary Vasodilator Response During Short-term Infusion of Prostacyclin in Primary Pulmonary Hypertension. Circulation 93, 484-488 (1996).
49. Roeleveld, R. J., et al. Effects of epoprostenol on right ventricular hypertrophy and dilatation in pulmonary hypertension. Chest 125, 572-579 (2004).
50. Safdar, Z. Outcome of pulmonary hypertension subjects transitioned from intravenous prostacyclin to oral bosentan. Respiratory medicine 103, 1688-1692 (2009).
51. Sánchez, M. A. G. & Torbicki, A. Foreword: right ventricular function and pulmonary hypertension. European Heart Journal Supplements 9, H3-H4 (2007).
52. Schattke, S., et al. Early right ventricular systolic dysfunction in patients with systemic sclerosis without pulmonary hypertension: a Doppler Tissue and Speckle Tracking echocardiography study. Cardiovascular Ultrasound 8, 3 (2010).
53. Sidhu M S, A. J., Saggar Rajan, Saggar Rajeev, Belperio J, Ardehali A, Ross D J. TRANSITION FROM PROSTANOID TO COMBINATION ORAL THERAPY FOR PULMONARY ARTERIAL HYPERTENSION. E-Journal of Cardiology 1, 8 (2011).

54. Simon, M. A. & Pinsky, M. R. Right Ventricular Dysfunction and Failure in Chronic pressure Overload. Cardiology Reseach and Practice 2011, 1 (2011).
55. Skoro-Sajer, N., et al. Pulmonary vascular reactivity and prognosis in patients with chronic thromboembolic pulmonary hypertension: a pilot study. Circulation 119, 298-305 (2009).
56. Steiner, M. K., et al. Conversion to bosentan from prostacyclin infusion therapy in pulmonary arterial hypertension: a pilot study. Chest. 130, 1471-1480. (2006).
57. Suleman, N. & Frost, A. E. Transition from epoprostenol and treprostinil to the oral endothelin receptor antagonist bosentan in patients with pulmonary hypertension. Chest. 126, 808-815. (2004).
58. Triantafyllou, K., Kranidis, A., Karabinos, E., Grassos, H. & Babalis, D. Clinical implications of the echocardiographic evaluation of right ventricular function on the long axis using newer techniques. Hellenic J Cardiol 51, 42-48 (2010).
59. Tayyareci, Y., et al. Early detection of right ventricular systolic dysfunction by using myocardial acceleration during isovolumic contraction in patients with mitral stenosis. Eur J Echocardiogr 9, 516-521 (2008).
60. Voelkel, N. F., et al. Right ventricular function and failure: report of a National Heart, Lung, and Blood Institute working group on cellular and molecular mechanisms of right heart failure. Circulation 114, 1883-1891 (2006).
61. van Wolferen, S. A., et al. Right ventricular reverse remodelling after sildenafil in pulmonary arterial hypertension. Heart 92, 1860-1861 (2006).
62. Vlahakes, G. J. Management of Pulmonary Hypertension and Right Ventricular Failure: Another Step Forward. Ann Thorac Surg 61, 1051-1052 (1996).
63. Zakir, R. M., Al-Dehneh, A., Maher, J., Saric, M. & Berkowitz, R. L. Right ventricular failure in patients with preserved ejection fraction and diastolic dysfunction: an underrecognized clinical entity. Congest Heart Fail 13, 164-169 (2007).
64. Gaine, S. P. & Rubin, L. J. Primary pulmonary hypertension. Lancet. 352, 719-725. (1998).

Each of the references above is incorporated by reference in its entirety.

What is claimed:

1. A method, comprising:
    identifying a patient being treated for pulmonary arterial hypertension with a parenteral prostanoid;
    determining that the patient is on a stable dose of the parenteral prostanoid;
    administering nitric oxide to the patient;
    determining that the patient does not have an enlarged right ventricle or right ventricular dysfunction based on a comparison of a hemodynamic parameter before nitric oxide is administered to the hemodynamics parameter after the nitric oxide is administered;
    weaning the patient off of the stable dose of parenteral prostanoid based on the pulmonary hypertension class of the patient and the determination that the patient does not have the enlarged right ventricle or right ventricular dysfunction; and
    transitioning from the parenteral prostanoid to an alternative therapy.

2. The method of claim 1, wherein the hemodynamic parameter is at least one of pulmonary vascular resistance, mean pulmonary arterial pressure, or cardiac output.

3. The method of claim 1, wherein determining that the patient does not have the enlarged right ventricle or right ventricular dysfunction includes identifying an increase in cardiac output after administration of the nitric oxide which correlates with a decrease in pulmonary vascular resistance after administration of the nitric oxide.

4. The method of claim 1, further comprising determining that the patient is in World Health Organization (WHO) pulmonary hypertension class I-III, the weaning the patient off the stable dose of parenteral prostanoid based on the patient being in WHO hypertension class I-III.

* * * * *